United States Patent
Itoh et al.

(10) Patent No.: US 6,440,117 B1
(45) Date of Patent: Aug. 27, 2002

(54) DISPOSABLE DIAPER HAVING UPSTANDING WALLS FOR IMPROVING LEAKAGE PREVENTION

(75) Inventors: Taketo Itoh; Hiroki Minowa, both of Tochigi-ken (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/496,270

(22) Filed: Feb. 1, 2000

(51) Int. Cl.$^7$ ................................................. A61F 13/15
(52) U.S. Cl. ............................ 604/385.28; 604/385.26; 604/385.27
(58) Field of Search ....................... 604/385.28, 385.21, 604/385.25, 385.01, 358, 385.26, 385.27, 385.23

(56) References Cited

U.S. PATENT DOCUMENTS

| | | | |
|---|---|---|---|
| 4,490,148 A | * 12/1984 | Beckestrom | 604/385 |
| 4,883,482 A | * 11/1989 | Gandrez et al. | 604/385.2 |
| 5,167,653 A | * 12/1992 | Igaue et al. | 604/385.2 |
| 5,582,606 A | * 12/1996 | Bruemmer et al. | 604/385.2 |
| 6,045,545 A | 4/2000 | Vandemoortele et al. | |
| 6,102,892 A | * 8/2000 | Putzner et al. | 604/101 |
| 6,103,952 A | * 8/2000 | Coles et al. | 604/358 |

FOREIGN PATENT DOCUMENTS

| | | |
|---|---|---|
| JP | 4152947 | 5/1992 |
| JP | 6209967 | 8/1994 |
| JP | 7-504094 | 5/1995 |
| JP | 7289583 | 7/1995 |
| JP | 08-215239 | 8/1996 |
| JP | 8215239 | 8/1996 |
| JP | 9024063 | 1/1997 |
| JP | 9173380 | 7/1997 |
| JP | 9271489 | 10/1997 |
| JP | 9276328 | 10/1997 |

\* cited by examiner

Primary Examiner—John G. Weiss
Assistant Examiner—Jacqueline F Stephens
(74) Attorney, Agent, or Firm—Birch, Stewart, Kolasch & Birch, LLP

(57) ABSTRACT

A disposable diaper includes an absorptive body having a liquid permeable topsheet, a liquid impermeable backsheet, and a liquid retentive absorbent member interposed between the sheets and a pair of flaps connected to the lateral edges of the absorptive body. The disposable diaper has a pair of upstanding walls which are formed by providing a sheet at the lateral sides of the diaper, the sheet has a lateral base edge and a lateral distal edge and is arranged in such a manner that the sheet is folded to allow the base edge and the distal edge to be positioned on the side of the flap and that the longitudinal ends of the sheet as folded are fixed to a stomach side section and a back side section of the diaper, respectively. The upstanding wall includes a base portion formed by fixing the sheet to the flap or the absorptive body; a folded portion positioned on the inner side of the absorptive body and formed by folding the sheet; and a free end portion positioned further outward in the width direction of the diaper than the folded portion, the folded portion and the free end portion are each provided with an elastic member to stand the upstanding wall upward.

2 Claims, 2 Drawing Sheets

DISPOSABLE DIAPER HAVING UPSTANDING WALLS FOR IMPROVING LEAKAGE PREVENTION

BACKGROUND OF THE INVENTION

1. Field of the Invention

The present invention relates to a disposable diaper with extremely excellent leakproofness.

2. Description of Background Art

Disposable diapers comprising a liquid permeable topsheet, a liquid impermeable backsheet, and a liquid retentive absorbent member interposed between the two sheets are widely used. Conventional disposable diapers contemplated for preventing leakage from the side portion of the crotch portion have a single upstanding wall formed of a strip of a sheet material. The upstanding wall is provided on the topsheet along each of the lateral edges of the absorbent member.

However, even the conventional disposable diapers with the upstanding wall have still been insufficient for leak prevention. Accordingly, the development of disposable diapers with improved leakproofness has been demanded.

SUMMARY OF THE INVENTION

Accordingly, an object of the present invention is to provide a disposable diaper having a more improved leakproofness than the conventional disposable diapers.

As a result of extensive investigations, the present inventors have found that the above object is accomplished by a disposable diaper having an upstanding wall along both of the lateral edges of the absorbent member. The upstanding wall has a folded portion and a free end portion with an elastic member being provided at the free end portion or at both of the folded portion and the free end portion.

The present invention, which has been completed based on this finding, provides in its first aspect a disposable diaper comprising:

an absorptive body including a liquid permeable topsheet, a liquid impermeable backsheet and a liquid retentive absorbent member interposed between the topsheet and the backsheet; and a pair of flaps connected to the lateral edges of the absorptive body, wherein:

the disposable diaper has a pair of upstanding walls which are formed by providing a sheet at the lateral sides of the diaper;

the sheet for forming the upstanding walls has a lateral base edge and a lateral distal edge and is arranged in such a manner that the sheet is folded to allow the lateral base edge and the lateral distal edge to be positioned on the side of the flap, and that the longitudinal ends of the sheet as folded are fixed to a stomach-side portion and a back-side portion of the diaper, respectively; and the upstanding wall includes a base portion formed by fixing the sheet to the flap or the absorptive body; a folded portion positioned on the inner side of the absorptive body and formed by folding the sheet; and a free end portion positioned further outward in the width direction of the diaper than the folded portion, the folded portion and the free end portion each being provided with an elastic member to stand the upstanding wall upward.

The present invention also provides in its second aspect a disposable diaper comprising:

an absorptive body including a liquid permeable topsheet, a liquid impermeable backsheet and a liquid retentive absorbent member interposed between the topsheet and the backsheet; and a pair of flaps connected to the lateral edges of the absorptive body, wherein:

the disposable diaper has a pair of upstanding walls which are formed by providing a sheet at the lateral sides of the diaper;

the sheet for forming the upstanding walls has a lateral base edge and a lateral distal edge and is arranged in such a manner that the sheet is folded to allow the lateral base edge and the lateral distal edge to be positioned on the side of the flap, and that the longitudinal ends of the sheet as folded are fixed to a stomach-side portion and a back-side portion of the diaper, respectively; and the upstanding wall includes a base portion formed by fixing the sheet to the flap or the absorptive body; a folded portion positioned on the inner side of the absorptive body and formed by folding the sheet; and a free end portion positioned further outward in the width direction of the diaper than the folded portion, while the folded portion is not provided with an elastic member, the free end portion is provided with an elastic member to stand the upstanding wall upward.

BRIEF DESCRIPTION OF THE DRAWINGS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
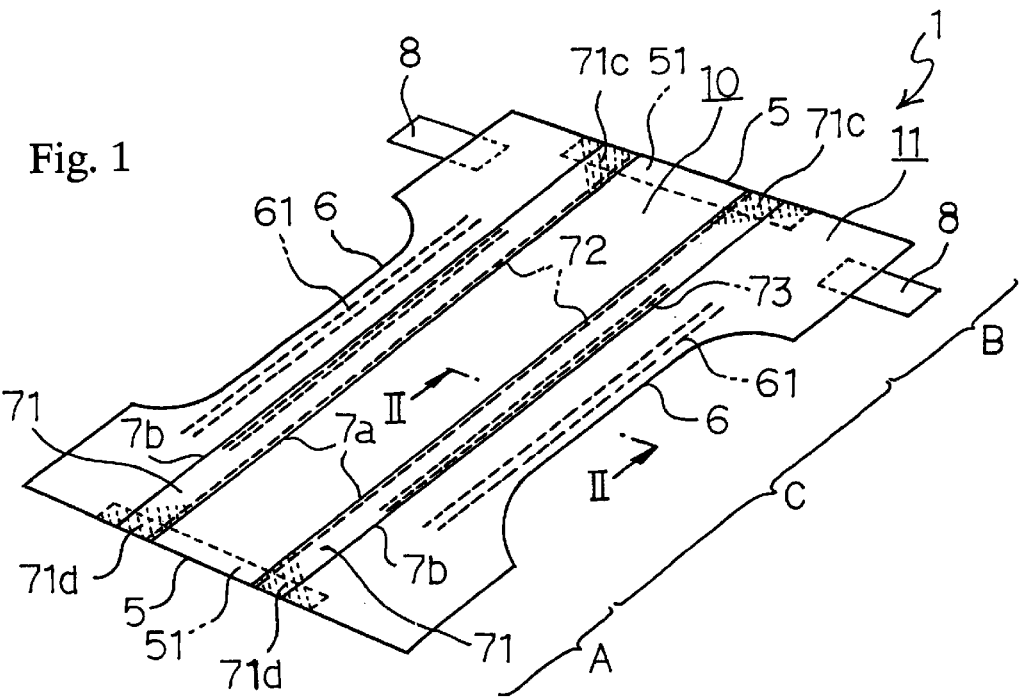
FIG. 1 is a perspective view showing an example of the disposable diaper according to the first aspect of the present invention.
Figure 2:
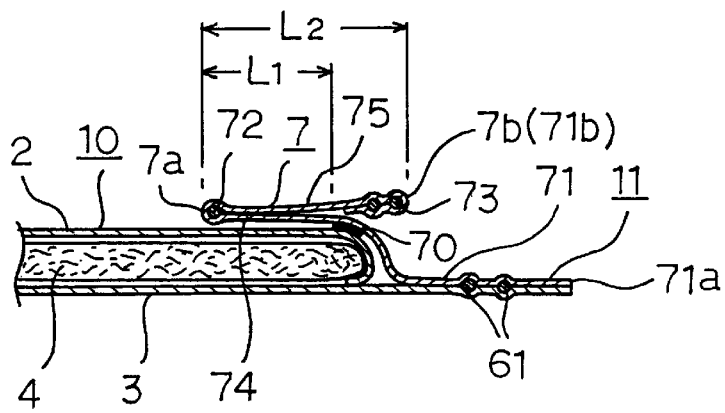
FIG. 2 is a cross sectional view of the disposable diaper shown in FIG. 1, taken along line II—II of FIG. 1.
Figure 3:
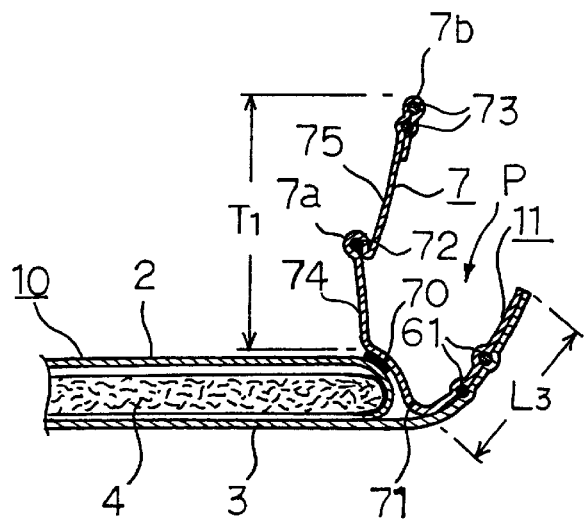
FIG. 3 is an enlarged cross sectional view showing the state of the disposable diaper shown in FIG. 2 while worn.

The present invention will be described hereunder with reference to the accompanying drawings. FIG. 1 is a perspective view showing an example of the disposable diaper according to the first aspect of the present invention; FIG. 2 is an enlarged cross sectional view of the disposable diaper shown in FIG. 1, taken along line II—II of FIG. 1; and FIG. 3 is an enlarged cross sectional view showing the state of the disposable diaper shown in FIG. 2 in use.

The disposable diaper 1 shown in FIGS. 1 and 2 comprises an absorptive body 10 having a liquid permeable topsheet 2, a liquid impermeable backsheet 3, and a liquid retentive absorbent member 4 interposed between the topsheet 2 and the backsheet 3, and a pair of flaps 11 connected to the lateral edges of the absorptive body 10.

The backsheet 3 of the disposable diaper 1 has its central portion narrowed to have the shape of a sandglass. The absorbent member 4 is smaller than the backsheet 3 and has a rectangular shape. The topsheet 2 is arranged so as to cover the upper surface and both sides of the absorbent member 4.

Each of the front and rear waist portions 5, 5 of the. diaper, 1 is provided with an elastic member 51 to make waist gathers.

The disposable diaper 1 is divided into a stomach side section A, a back side section B, and a crotch section C that is between the sections A and B. A fastening tape 8 is provided on each side of the back side section B. That is, the disposable diaper of this embodiment is a flat type disposable diaper. Leg portions 6 positioned on both sides of the crotch section C are located around the wearer's legs while the diaper is worn. The leg portions 6 are provided with an elastic member 61 to form leg gathers.

The flaps 11 are each formed of the backsheet 3, a sheet 71 for forming upstanding walls which extend outward from the side edges of the absorbent member 4, and the leg portion elastic member 61 sandwiched in between the sheets 3 and 71 as hereinafter described.

The topsheet 2, backsheet 3, absorbent member 4, elastic members 51 and 61, and fastening tapes 8 can be of any materials commonly used in disposable diapers. The structure made up of these members is the same as employed in conventional disposable diapers.

In the disposable diaper 1 according to the embodiment shown in FIGS. 1 and 2, a pair of upstanding walls 7 are formed by providing the sheet 71 for forming the upstanding walls at the lateral sides of the diaper 1. The sheet 71 is folded in such a manner that the lateral base edge 71 a and the lateral distal edge 71b are positioned on the side of the flap 11. The longitudinal front and rear ends 71c and 71d of the sheet, when folded, are fixed to the back side section B and the stomach side section A, respectively. The upstanding wall has a base portion 70, a folded portion 7a and a free end portion 7b. The base portion 70 is formed by fixing the sheet 71 to the flap 11 on the inner side of the diaper, i.e., on the side inward to the longitudinal center of the diaper. The folded portion 7a is positioned on the side inward to the longitudinal center of the absorptive body 10 and is formed by folding the sheet 71. The free end portion 7b is positioned more outward in the width direction of the diaper than the folded portion 7a. The folded portion 7a and the free end portion 7b are provided with elastic members 72 and 73, respectively, so that the upstanding wall can stand upward.

The free end portion 7b is positioned more outward in the width direction of the diaper 1 than the folded portion 7a not only in a developed state as illustrated in FIGS. 1 and 2 where each gather is tensed, but in a state under no stress. The state "under no stress" means that no outer force (tension) is applied to the diaper 1, allowing the sheet 71 to gather.

The base portion 70 of the upstanding wall 7 is a portion at which the upstanding wall 7 is fixed to the absorptive body 10. The base portion 70 is positioned on the absorbent member 4 of the absorptive body 10 and more inward in the width direction of the diaper than the elastic member 61 of the leg portion.

It is preferred that the length $L_3$ of the flap 11 in the crotch section be smaller than the height $T_1$ of the upstanding wall 7 as shown in FIG. 3. The length $L_3$ of the flap 11 is preferably 10 to 50 mm, and the height $T_1$ of the upstanding wall 7 is preferably 15 to 80 mm, so that the length $L_3$ is preferably smaller than the height $T_1$ by 5 to 30 mm.

As shown in FIG. 2, the upstanding wall 7 located on each side of the diaper 1 is formed of a single sheet 71. The sheet 71 for forming the upstanding wall is arranged to cover the area from the lateral edge of the leg portion 6 up to the lateral side of the absorbent member 4 including the lateral edge thereof and adhered to the topsheet 2 at the base portion 70. The portion of the sheet 71 which is positioned more inward in the width direction of the diaper 1 than the base portion 70 is folded along a folded line, which is along the longitudinal direction of the diaper, toward the width direction of the diaper via the upper side of the diaper (upper side of the topsheet 2), to form a folded portion 7a. The upstanding wall 7, being thus constructed, is sectioned into a lower wall portion 74 which is between the base portion 70 and the folded portion 7a and an upper wall portion 75 which is between the folded portion 7a and the free end portion 7b. Because the lower wall portion 74 and the upper wall portion 75 are in the free state, not being fixed to other members (such as the topsheet or backsheet), these two portions stand upward integrally and continuously to form a leakproof wall while the diaper 1 is worn.

The sheet 71 forming the upstanding wall has a lateral base edge 71a and a lateral distal edge 71b at the lateral edges thereof The position of the base edge 71a agrees with the position of the lateral edge of the backsheet 3. The distal edge is positioned on the side of the flap 11 rather than the side of the lateral edge of the absorbent member 4. The sheet 71 forming the upstanding wall is arranged to cover the side of the absorbent member 4, to laterally extend from the lateral edge of the absorbent member 4 to cover the leg portion 6, and the be fixed to the backsheet 3. The elastic member 61 of the leg portion are thus held and fixed between the backsheet 3 and the sheet 71.

The entire longitudinal end portions of the sheet 71 are connected and fixed, in their folded state, to the topsheet 2 and the backsheet 3 in the back side section B and the stomach side section A. Therefore, the upstanding wall 7 is not formed in the back side section B and the stomach side section A. In other words, the upstanding wall 7 does not need to be formed .over the whole length of the disposable diaper 1. It is just enough that the upstanding wall 7 is formed in at least the crotch portion C.

At the folded portion 7a, the lower wall portion 74 and the upper wall portion 75 adhere around an elastic member 72 so that the entire surface of the elastic member 72 may be covered with the sheet 71. At the free end portion 7b, the sheet 71 is folded back so that the surface of the elastic members 73 may be covered with the sheet 71, and the folded end portion of the sheet 71 may be adhered to the upper wall portion 75.

The length $L_1$ of the lower wall portion 74 is preferably 10 to 40 mm, still preferably 20 to 30 mm. The length $L_2$ of the upper wall portion 75 is preferably 5 to 60 mm, still preferably 20 to 30 mm. It is arbitrary which of the length $L_1$ of the lower wall portion 74 and the length $L_2$ of the upper wall portion 75 is longer than the other.

As shown in FIG. 2, the base portion 70 is formed by fixing the sheet 71 onto the topsheet 2 by heat sealing. It is preferred that the base portion 70 be either in linear or curved forms and have a width of 2 to 20 mm.

The sheet 71 for forming the upstanding wall can be of water-repellent nonwoven fabric, and the like. Any water-repellent nonwoven fabric that is customarily used in absorbent articles including disposable diapers can be employed with no particular limitation. Specific examples of useful materials of the sheet 71 include nonwoven fabric fabricated from the following materials in accordance with the following methods. Material: Water-repellent fibers that can be fabricated into a nonwoven fabric including filaments comprising a single resin such as a thermoplastic resin, e.g., polyethylene, polypropylene, polyethylene terephthalate and polyamide, and conjugated filaments having a core/shell structure, a side-by-side structure, and the like. Fabrication method: Spun-bond system, binder system, water needling system, needle punch system, and the like. Specifically, systems in which filaments obtained by coventional melt spinning, if necessary drawn and crimped, are cut into staple fibers, and the staple fibers are point-bonded by heat or with an adhesive, etc. or entangled by means of water jets, needles, etc., i.e., the wet process, the dry process, the spun-lacing method, the spun-bonding method, and the like.

The nonwoven fabric made of split filaments obtained by splitting multilayer filaments by an outer, force, and a melt-blown nonwoven fabric can also be used.

The disposable diaper 1 of this embodiment can be used in the same manner as conventional disposable diapers of flat type. On use of the disposable diaper 1 of this embodiment, as shown in FIG. 3, the lower wall portion 74 stands up with a slight lean with its inner side in the width direction of the diaper 1 coming further up than its outer side in the width direction thereof. On the other hand, the upper wall portion 75 stands up with a slight lean with its outer side in the width direction of the diaper 1 coming further up than its inner side in the width direction thereof. As a result, the upstanding wall 7 stands almost upright as a whole while slightly forming a dog-legged shape. The flaps 11 also stand upward by the action of the leg gathers.

Having the above-described structure, the upstanding wall 7 stops body fluids at the lower wall portion 74. If body fluids go up over the lower wall portion 74, the fluids are effectively stopped by the upper wall portion 75. While simple inward-leaning standing walls conventionally used sometimes cause absorption obstruction, according to the disposable diaper of this embodiment having the above-described structure, the upstanding wall does not cover the upper side of the absorbent member more than necessary in use so that the absorption is not hindered. In the case of the conventional disposable diapers having a simple outward-leaning leakproof wall, waste fluid such as urine that is excreted fast sometimes flows over the wall. Such a disadvantage does not arise with the present embodiment of the invention because the lower wall portion leans inward in the width direction of the diaper.

By standing upward in the manner described, the upstanding wall 7 provides an improved fit to a wearer and assures an increased contact area of the members constituting the diaper with the wearer to improve leakproofness. Should waste fluid flow over the wall 7, it would be received by a pocket P formed by the wall 7 and the flap 11, which presents a further advantage of leakproofness. Furthermore, the upstanding wall 7, being constituted in the above-described manner, does not interfere with the function of the leg gathers and manages to prevent leakage from the side portion in cooperation with the leg gathers. Furthermore, with the length $L_3$ of the flap 11 being shorter than the height $T_1$ of the upstanding wall 7, the upstanding wall 7 would effectively turn inward to the diaper to enhance the advantageous effects as desired while the diaper 1 is being worn. In short, in the disposable diaper 1 according to this embodiment, since the upstanding wall 7 is constituted as described above and stands upward with a slight lean while worn, fit to the wearer is excellent compared with disposable diapers having conventional leakproof walls, and as a result improved leakproofness is exhibited.

The disposable diaper according to the embodiment is produced by, a conventional method including joining the topsheet 2 and the backsheet 3 while interposing the absorbent member 4 therebetween to form and fix the members other than the upstanding wall, folding the sheet 71 as mentioned above while interposing the elastic members 72 and 73 between the folds, and heat-sealing a predetermined area to form the base portion 70.

Specifically, after an absorptive body having the backsheet extended outward on both lateral edges is prepared in a conventional manner, an upstanding wall is formed by a method comprising the steps of (1) disposing, an elastic member at one end of a sheet for forming an upstanding wall to form a free end portion, (2) folding the sheet having the free end portion while inserting an elastic member in the fold to form a folded portion, (3) adhering the longitudinal ends of the folded sheet having the free end portion and the folded portion, (4) adhering the flap side portion of the folded sheet to the flap of the absorptive body, and (5) fixing the longitudinal ends of the folded sheet to the absorptive body.

Figure 4:
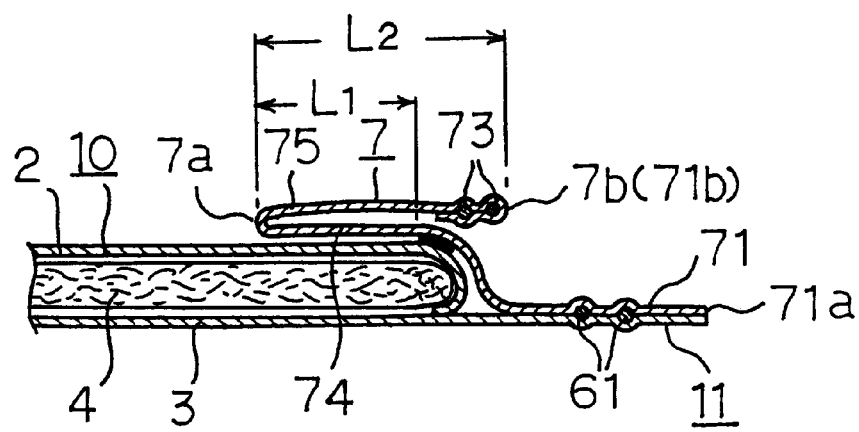
FIG. 4 is a cross sectional view showing an example of the disposable diaper according to the second aspect of the present invention, corresponding to FIG. 2 according to the first aspect of the present invention.
Figure 5:
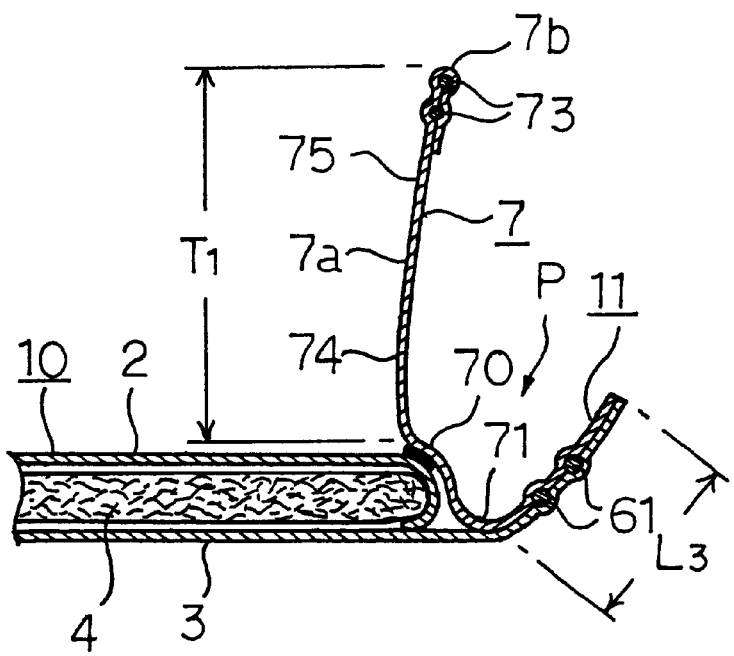
FIG. 5 is an enlarged cross sectional view showing the state of the disposable diaper shown in FIG. 4 while worn, corresponding to FIG. 3 according to the first aspect of the present invention.

The disposable diaper according to the second aspect of the present invention will now be illustrated with reference to FIGS. 4 and 5. The description given hereinabove with respect to the same particulars as the first aspect of the invention applies appropriately to the second aspect so that only the difference from the first aspect will be described. In FIGS. 4 and 5, the same members as used in FIGS. 1 to 3 are given the same numeral references.

As shown in FIGS. 4 and 5, the difference of the second aspect from the first one is that the folded portion 7a, which is formed by folding the sheet 71 and positioned on the inner side of the aborptive body 10, is not provided with an elastic member. That is, only the free end portion 7b is provided with elastic members 73 to stand the upstanding wall 7 upward.

As illustrated in FIG. 5, while the diaper is worn, the lower wall portion 74 of the upstanding wall 7 stands up with a slight lean, and the upper wall portion 75 stands up with a slight lean with its outer side in the width direction of the diaper 1 coming further up than its inner side. As a result, the upstanding wall 7 stands almost upright as a whole. The disposable diaper according to the second aspect exhibits improved leakproofness similarly to the one according to the first aspect.

It should be understood that the disposable diaper according to the present invention is not construed as being limited to the above-described embodiments, and various changes and modifications can be made therein without departing from the spirit and scope thereof. For example, the upstanding wall 7 in each embodiment can be formed over the whole length of the disposable diaper 1. The base portion 70 may be curved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

As described, the disposable diaper according to the present invention has improved leakproofness compared with conventional disposable diapers.

What is claimed is:

1. A disposable diaper comprising:

an absorptive body including a liquid permeable topsheet, a liquid impermeable backsheet and a liquid retentive absorbent member interposed between said topsheet and said backsheet;

a pair of flaps connected to lateral edges of said absorptive body;

a pair of upstanding walls, each of said pair of upstanding walls being formed by providing a sheet at lateral sides of said diaper, each of said sheets for forming said upstanding walls having a lateral base edge and a lateral distal edge and being arranged in such a manner that said sheet is folded to allow said lateral base edge and said lateral distal edge to be positioned on a side of a respective of said pair of flaps, and longitudinal ends of said sheet, when folded, are fixed to a stomach-side portion and a back-side portion of said diaper, respectively; and each of said upstanding walls includes a base portion formed by fixing said sheet to said flap or said absorptive body; a folded portion positioned further inward than said base portion and formed by folding said sheet; and a free end portion positioned further outward in the width direction of the diaper than said folded portion and said base portion, said folded portion and said free end portion each being provided with an elastic member to stand said upstanding wall upward, and wherein each of said pair of flaps is formed by said sheets for forming said upstanding walls and said backsheet.

2. A disposable diaper comprising:

an absorptive body including a liquid permeable topsheet, a liquid impermeable backsheet and a liquid retentive absorbent member interposed between said topsheet and said backsheet;

a pair of flaps connected to lateral edges of said absorptive body;

a pair of upstanding walls each of said pair of upstanding walls being formed by providing a sheet at lateral sides of said diaper, each of said sheets for forming said upstanding walls having a lateral base edge and a lateral distal edge and being arranged in such a manner that said sheet is folded to allow said lateral base edge and said lateral distal edge to be positioned on a side of a respective of said pair of-flaps, and longitudinal ends of said sheet, when folded, are fixed to a stomach-side portion and a back-side portion of said diaper, respectively; and each of said upstanding walls includes a base portion formed by fixing said sheet to said flap or said absorptive body; a folded portion positioned further inward than said base portion and formed by folding said sheet; and a free end portion positioned further outward in the width direction of the diaper than said folded portion and said base portion, said folded portion not being provided with an elastic member, said free end portion being provided with an elastic member to stand the upstanding wall upward, and wherein each of said pair of flaps is formed by said sheets for forming said upstanding walls and said backsheet.

* * * * *